United States Patent
Lange et al.

(10) Patent No.: US 10,525,001 B2
(45) Date of Patent: Jan. 7, 2020

(54) PRODUCT AND METHOD FOR THE TEMPORARY SHAPING OF KERATIN-CONTAINING FIBERS

(71) Applicant: Henkel AG & Co. KGaA, Duesseldorf (DE)

(72) Inventors: Julia Bibiane Lange, Bad Bramstedt (DE); Anna Puls, Winsen (DE); Cyrielle Martinez, Hamburg (DE); Bernd Richters, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 15/555,976

(22) PCT Filed: Nov. 11, 2015

(86) PCT No.: PCT/EP2015/076325
§ 371 (c)(1),
(2) Date: Sep. 6, 2017

(87) PCT Pub. No.: WO2016/142009
PCT Pub. Date: Sep. 15, 2016

(65) Prior Publication Data
US 2018/0055756 A1      Mar. 1, 2018

(30) Foreign Application Priority Data
Mar. 9, 2015   (DE) ................. 10 2015 204 150

(51) Int. Cl.
*A61K 8/81* (2006.01)
*A61Q 5/06* (2006.01)
*A61K 8/41* (2006.01)

(52) U.S. Cl.
CPC .......... *A61K 8/8152* (2013.01); *A61K 8/8147* (2013.01); *A61K 8/8176* (2013.01); *A61K 8/8182* (2013.01); *A61Q 5/06* (2013.01); *A61K 2800/594* (2013.01)

(58) Field of Classification Search
CPC ............ A61K 2800/594; A61K 8/8152; A61K 8/8182; A61Q 5/06
See application file for complete search history.

(56) References Cited

U.S. PATENT DOCUMENTS

| 6,190,647 | B1 | 2/2001 | Karlen et al. |
| 2011/0135589 | A1 | 1/2011 | Knappe et al. |
| 2014/0093467 | A1* | 4/2014 | Knappe ................ A61K 8/8152 424/70.15 |
| 2018/0049967 | A1* | 2/2018 | Lange ...................... A61Q 5/06 |
| 2018/0168989 | A1* | 6/2018 | Lange .................. A61K 8/8152 |

FOREIGN PATENT DOCUMENTS

| DE | 102007008089 A1 | 8/2008 | |
| DE | 102011077364 | * 10/2011 | ............... A61K 8/81 |
| DE | 102013225753 A1 | 5/2014 | |
| EP | 1238646 A1 | 9/2002 | |
| WO | WO 2010/020503 | * 2/2010 | |

OTHER PUBLICATIONS

EPO, International Search Report and Written Opinion issued in International Application No. PCT/EP2015/076325, dated Jan. 7, 2016.
BASF, "Acrylic Terpolymer Products for Hair-Setting Preparations With a Strong, Long-Lasting Effect (Luvimer)", Sep. 2000.
Jones, Charles, "Multifunctional Synthetic Rheology Modifiers for Personal Care Formulations: More Than Just Thickeners", 2005, Rohm and Haas Company.
Signori, Vittoria, "Acrylates Copolymers—Why do we Need to Neutralize them?", 2006, Cosmetic Science Technology.

* cited by examiner

*Primary Examiner* — Anna R Falkowitz
(74) *Attorney, Agent, or Firm* — Lorenz & Kopf, LLP

(57) ABSTRACT

The invention relates to a cosmetic composition for the temporary shaping of hair, comprising a combination of two specific anionic acrylate copolymers. The cosmetic composition provides an extremely good moisture resistance.

10 Claims, No Drawings

PRODUCT AND METHOD FOR THE TEMPORARY SHAPING OF KERATIN-CONTAINING FIBERS

CROSS-REFERENCE TO RELATED APPLICATION

This application is a U.S. National-Stage entry under 35 U.S.C. § 371 based on International Application No. PCT/EP2015/076325, filed Nov. 11, 2015, which was published under PCT Article 21(2) and which claims priority to German Application No. 10 2015 204 150.6, filed Mar. 9, 2015, which are all hereby incorporated in their entirety by reference.

TECHNICAL FIELD

The present disclosure relates to a cosmetic composition for the temporary shaping of keratin-containing fibers, particularly human hair, wherein the composition contains a combination of two anionic acrylate polymers.

BACKGROUND

Temporary shaping of hairstyles for a lengthy period extending to a number of days generally requires the application of setting agents. Hair treatment agents, which are used for temporarily shaping the hair, therefore have an important role to play. Suitable agents for temporary shaping usually contain synthetic polymers and/or waxes as the setting agent. Agents for supporting a temporary shaping of keratin-containing fibers can be made up as hairspray, hair wax, hair gel or hair mousse, for instance.

The most important characteristic of an agent for temporarily shaping hair, also referred to below as a styling product, is in giving the fibers treated the strongest possible hold in the newly modeled form—i.e. a form into which the hair has been styled. This is referred to as a strong style hold or high degree of hold by the styling agent. Hairstyle hold is substantially determined by the type and quantity of the setting agent used, wherein, however, the further components of the styling product can also have an influence.

In addition to having a high degree of hold, styling products must meet a number of other requirements. This can be roughly divided into characteristics on the hair, characteristics of the specific formulation, for example characteristics of the mousse, the gel or the sprayed aerosol, and characteristics that relate to handling of the styling product, wherein the characteristics on the hair are of particular importance. Moisture resistance, low adhesion (tack) and a well-balanced conditioning effect should be mentioned in particular. Furthermore, a styling product should, as far as possible, be universally applicable to all hair types and mild on the hair and skin.

A plurality of synthetic polymers have already been developed as setting agents for use in styling products to meet the various requirements. The polymers can be classified into cationic, anionic, nonionic and amphoteric setting polymers. Ideally, the polymers, when applied to the hair, result in a polymer film which, on the one hand, gives the hairstyle a strong hold, but on the other hand is sufficiently flexible not to break when under stress. What are known as film plaques are formed even if the polymer film is too brittle; these are residues which break off when the hair moves and give the impression that the user of such a styling product has dandruff. Similar problems arise when waxes are used as the setting agent in the styling product. If the styling product is a gel or a paste, the polymers should additionally possess thickening properties.

Known anionic polymers used in hair strengthening products are acrylate copolymers with two or more structural units. Certain copolymers of this kind with the INCI designation acrylates/steareth-20 methacrylate copolymer are described in European Patent EP 897 711 B1 as a component of hair cosmetic agents for temporarily shaping hair.

Further copolymers of this nature with the INCI designation acrylates/beheneth-25 methacrylate copolymer and the use thereof in cosmetic compositions for the temporary shaping of keratinous fibers are described in German application DE 10 2008 038 105 A1.

Furthermore, hydrophobically modified acrylate copolymers (INCI: acrylates copolymer (and) water) are commercially available and essentially act as thickening agents. The AquaStyle® SH-100 Polymer datasheet (Ashland Inc.) describes an acrylate copolymer of this kind and its use in combination with carbomers. Suitability for crystal-clear hair gels, good initial stiffness, moisture resistance and a long-term effect are described.

One problem addressed by the present disclosure would be to provide further suitable polymer combinations which are exemplified by good film-forming and/or setting characteristics, have a very high degree of hold without having to sacrifice flexibility, and good moisture resistance—particularly resistance to sweat and water—and additionally be suitable for the production of stably viscous and stably transparent cosmetic compositions. In particular, styling products currently available can be further improved in that a good combination of stiffness and high humidity curl retention is not always sufficiently ensured. The problem addressed by the present disclosure is therefore to provide styling products of this kind which, in particular, result in both good stiffness and good curl retention, in addition to the characteristics described above.

BRIEF SUMMARY

A cosmetic composition for the temporary shaping of keratinous fibers is provided herein. The cosmetic composition includes at least one amphiphilic, anionic acrylate copolymer (a). The at least one amphiphilic, anionic acrylate copolymer (a) includes at least one structural unit (a1) and at least one structural unit (a2),

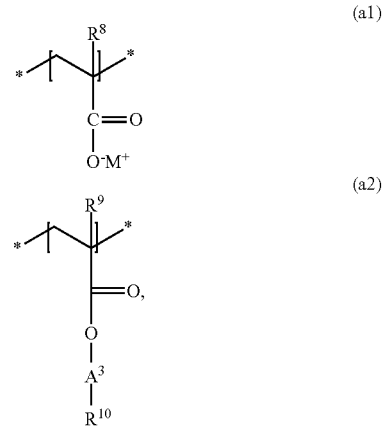

wherein

R⁸ and R⁹ are, independently of one another, a hydrogen atom or a methyl group,

R¹⁰ is a (C₈ to C₃₀) alkyl group,

M⁺ is a physiologically tolerable cation, and

A³ is;

a group *—(CH₂CH₂O)ₓ—*, wherein x is an integer number from 5 to 35, a group *—(CH₂CHMeO)ᵧ—*, wherein y is an integer number from 5 to 35, or a group *—(CH₂CH₂O)ₓ—(CH₂CHMeO)ᵧ—*, wherein the sum x+y is an integer number from 5 to 35 and x and y are greater than zero.

The cosmetic composition further includes at least one anionic acrylate copolymer (b). The at least one anionic acrylate copolymer (b) is built up of at least the following monomer units: (b1) at least one (meth)acrylic acid unit, (b2) at least one (meth)acrylic acid ethyl ester unit, and (b3) at least one (meth)acrylic acid ester unit. The at least one (meth)acrylic acid ester unit (b3) differs from (meth)acrylic acid ethyl ester unit (b2) and includes one hydrophobic group as an ester group.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

This was achieved as contemplated herein by a combination of two, specific anionic acrylate polymers which differ from one another.

The present disclosure provides:

1. A cosmetic composition for the temporary shaping of keratinous fibers, comprising:

(a) at least one amphiphilic, anionic acrylate copolymer (a), comprising at least one structural unit (a1) and at least one structural unit (a2),

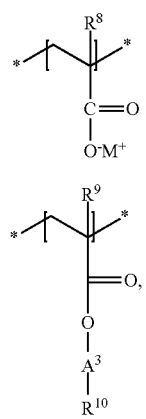

(a1)

(a2)

wherein

R⁸ and R⁹ are, independently of one another, a hydrogen atom or a methyl group, R¹⁰ is a (C⁸ to C³⁰) alkyl group, M⁺ is a physiologically tolerable cation and A³ is a group *—(CH₂CH₂O)ₓ—*, wherein x is an integer number from 5 to 35, a group *—(CH₂CHMeO)ᵧ—*, wherein y is an integer number from 5 to 35 or a group *—(CH₂CH₂O)ₓ—(CH₂CHMeO)ᵧ—*, wherein the sum x+y is an integer number from 5 to 35 and x and y are greater than zero and (b) at least one anionic acrylate copolymer (b) different from the acrylate copolymer (a), which anionic acrylate copolymer is made up of at least the following monomer units:

(b1) at least one (meth)acrylic acid unit (b2) at least one (meth)acrylic acid ethyl ester unit (b3) at least one (meth)acrylic acid ester unit which is different from the (meth)acrylic acid ethyl ester unit (b2) and comprises a hydrophobic group as an ester group.

2. Cosmetic composition in accordance with paragraph 1, wherein the at least one amphiphilic anionic acrylate copolymer (a) comprises at least one structural unit of the formula (a1-1), at least one structural unit of the formula (a1-2) and at least one structural unit of the formula (a2-1)

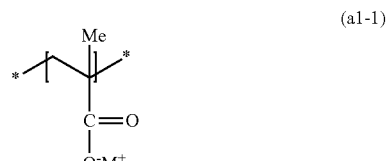

(a1-1)

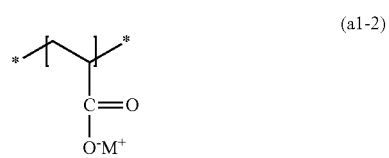

(a1-2)

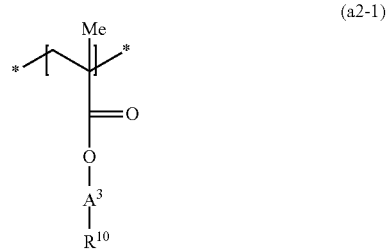

(a2-1)

wherein

M⁺ is, independently of one another, a physiologically tolerable cation, R¹⁰ is a (C₈ to C₃₀) alkyl group and A³ is a group *—(CH₂CH₂O)ₓ—*, wherein x is an integer number from 5 to 35, particularly from 15 to 30.

3. Cosmetic composition in accordance with one of the preceding paragraphs, wherein the at least one amphiphilic anionic acrylate copolymer (a) comprises at least one structural unit (a1) and at least one structural unit (a2),

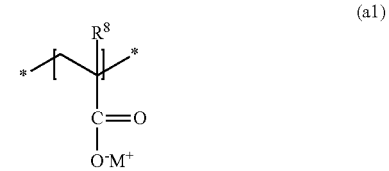

(a1)

-continued

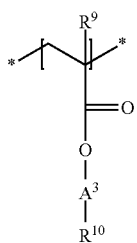

wherein
R⁸ is a hydrogen atom or a methyl group,
R⁹ is a methyl group
R¹⁰ is an octadecyl group (stearyl group),
M⁺ is a physiologically tolerable cation and
A³ is a group *—(CH₂CH₂O)ₓ—*, wherein x is an integer number from 20.

4. Cosmetic composition in accordance with paragraphs 1 or 2, wherein the at least one amphiphilic anionic acrylate copolymer (a) comprises at least one structural unit (a1) and at least one structural unit (a2),

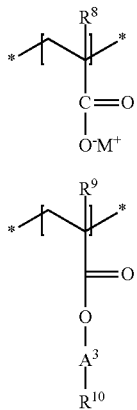

wherein
R⁸ is a hydrogen atom or a methyl group,
R⁹ is a methyl group
R¹⁰ is a docosyl group (behenyl group),
M⁺ is a physiologically tolerable cation and
A³ is a group *—(CH₂CH₂O)ₓ—*, wherein x is an integer number from 25.

5. Cosmetic composition in accordance with one of the preceding paragraphs, wherein the composition contains copolymer (a) in a fraction of from about 0.05 to about 5.0 wt. %, preferably from about 0.1 to about 4.0 wt. %, further preferably from about 0.2 to about 2.0 wt. %, related to the total weight of the cosmetic composition.

6. Cosmetic composition in accordance with one of the preceding paragraphs, wherein the anionic acrylate copolymer (b) comprises methacrylic acid as monomer unit (b1) and ethyl acrylate as monomer unit (b2).

7. Cosmetic composition in accordance with one of the preceding paragraphs, wherein the anionic acrylate copolymer (b) comprises a (meth)acrylic acid alkyl ester as monomer unit (b3).

8. Cosmetic composition in accordance with one of the preceding paragraphs, wherein the composition contains the anionic acrylate copolymer (b) in a fraction of from about 0.05 to about 5.0 wt. %, preferably from about 0.5 to about 4.0 wt. %, further preferably from about 1.0 to about 3.0 wt. %, related to the total weight of the cosmetic composition.

9. Cosmetic composition in accordance with one of the preceding paragraphs, wherein the anionic acrylate copolymer (b) with a solids content of 2 wt. % in an aqueous neutralized solution at 25° C. has a viscosity of from about 60000 to about 120000 cPs.

10. Cosmetic composition in accordance with one of the preceding paragraphs, wherein the anionic acrylate copolymer (a) is a copolymer with the INCI designation acrylates/steareth-20 methacrylate copolymer, particularly Aculyn® 22 (Rohm&Haas).

11. Cosmetic composition in accordance with one of paragraphs 1 to 8, wherein the anionic acrylate copolymer (a) is a copolymer with the INCI designation acrylates/beheneth-25 methacrylate copolymer, particularly Aculyn® 28 (Rohm&Haas).

12. Cosmetic composition in accordance with one of the preceding paragraphs, wherein the anionic acrylate copolymer (b) is a copolymer with the INCI designation acrylates copolymer (and) water, particularly AquaStyle SH-100 (Ashland Inc.).

13. Cosmetic composition in accordance with one of the preceding paragraphs, which, related to the total weight of the cosmetic composition, contains:
From about 0.05 to about 5.0 wt. % of the anionic acrylate copolymer (a), and from about 0.05 to about 5.0 wt. % of the anionic acrylate copolymer (b).

14. Cosmetic composition in accordance with one of the preceding paragraphs, comprising, related to the total weight of the cosmetic composition:
from about 0.2 to about 2.0 wt. % of the anionic acrylate copolymer (a),
and from about 1.0 to about 3.0 wt. % of the anionic acrylate copolymer (b).

15. Cosmetic composition in accordance with one of the preceding paragraphs, wherein the composition further contains at least one polymer (c) which differs from the acrylate copolymers (a) and (b), particularly an anionic or nonionic polymer (c).

16. Cosmetic composition in accordance with one of the preceding paragraphs, wherein, related to the total weight of the cosmetic composition, it further contains
c) from about 1.0 to about 10 wt. % polyvinylpyrrolidone and/or vinylpyrrolidone/vinyl acetate copolymer, preferably polyvinylpyrrolidone.

17. Cosmetic composition in accordance with paragraph 16, wherein the weight fraction of the polyvinylpyrrolidone and/or vinylpyrrolidone/vinyl acetate copolymer c) of the total weight of the cosmetic composition is from about 2.0 to about 8.5 wt. %, preferably from about 3.0 to about 7.0 wt. %.

18. Cosmetic composition in accordance with one of the preceding paragraphs, wherein the composition contains water in a fraction of from about 50 to about 95 wt. %, preferably between about 60 and about 90 wt. %, particularly between about 65 and about 85 wt. %, related to the total weight of the cosmetic composition.

19. Cosmetic composition in accordance with one of the preceding paragraphs, wherein the composition takes the form of hair gel, hair spray, hair mousse or hair wax, particularly of hair gel.

20. Use of a cosmetic composition according to one of the paragraphs 1 to 19 for the temporary shaping of keratinous fibers.

21. Use of a cosmetic composition according to one of the paragraphs 1 to 19 for improving the moisture resistance of temporarily shaped keratinous fibers.

22. Method for temporarily shaping keratinous fibers, particularly human hair, in which the cosmetic composition according to one of the paragraphs 1 to 19 is applied to keratinous fibers.

It was surprisingly established within the scope of the present disclosure that an improved moisture resistance of styling products can be obtained by the combination of two, per se, known components that are already used in styling products. Other characteristics usually required of styling products such as long-term curl hold, stiffness and low tack are still retained. A good combination of characteristics of this nature was not to be expected, even with knowledge of the individual components, and was surprising. It has been found in experiment that a strongly super-additive, that is to say synergistic, effect was obtained in respect of moisture resistance, which manifested itself in the HHRC test (High Humidity Curl Retention test), by the combination of the two components.

The concept of keratinous fibers comprises, as contemplated herein, furs, wool and feathers, but particularly human hair.

The essential components of the cosmetic composition as contemplated herein are the amphiphilic, anionic acrylate copolymer (a) and the anionic acrylate copolymer (b) which is different from acrylate copolymer (a).

The amphiphilic anionic acrylate copolymer (a) comprises at least one structural unit (a1) and at least one structural unit (a2),

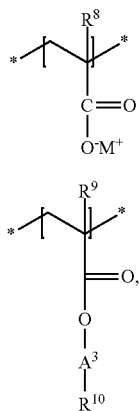

wherein
$R^8$ and $R^9$ are, independently of one another, a hydrogen atom or a methyl group,
$R^{10}$ is a ($C_8$ to $C_{30}$) alkyl group,
M+ is a physiologically tolerable cation and
$A^3$ is
  a group *—$(CH_2CH_2O)_x$—*, wherein x is an integer number from 5 to 35,
  a group *—$(CH_2CHMeO)_y$—*, wherein y is an integer number from 5 to 35 or
  a group *—$(CH_2CH_2O)_x$—$(CH_2CHMeO)_y$—*, wherein the sum x+y is an integer number from 5 to 35 and x and y are greater than zero.

Examples of (C8 to C30) alkyl groups as contemplated herein are octyl (capryl), decyl (caprinyl), dodecyl (lauryl), tetradecyl (myristyl), hexadecyl (cetyl), octadecyl (stearyl), eicosyl (arachyl), docosyl (behenyl).

It is preferred as contemplated herein if the amphiphilic anionic polymers (a) are selected from the group of copolymers which comprise at least one structural unit of the formula (a1-1), at least one structural unit of the formula (a1-2) and at least one structural unit of the formula (a2)

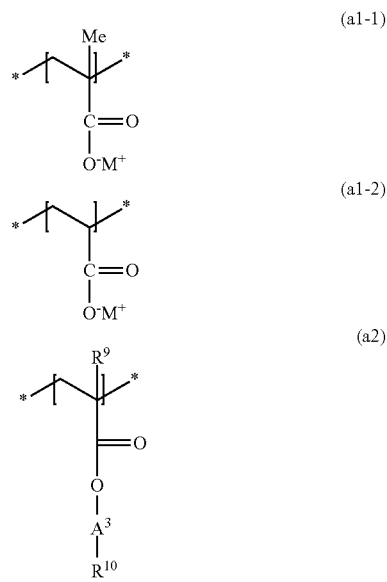

wherein
$M^+$ is independently of one another a physiologically tolerable cation,
$R^9$ is a hydrogen atom or a methyl group (preferably a methyl group),
$R^{10}$ is a ($C_8$ to $C_{30}$) alkyl group (particularly octyl (capryl), decyl (caprinyl), dodecyl (lauryl), tetradecyl (myristyl), hexadecyl (cetyl), octadecyl (stearyl), eicosyl (arachyl) or docosyl (behenyl),
$A^3$ is
  a group *—$(CH_2CH_2O)_x$—*, wherein x is an integer number from 5 to 35,
  a group *—$(CH_2CHMeO)_y$—*, wherein y is an integer number from 5 to 35 or
  a group *—$(CH_2CH_2O)_x$—$(CH_2CHMeO)_y$—*, wherein the sum x+y is an integer number from 5 to 35 and x and y are greater than zero (preferably a group *—$(CH_2CH_2O)_x$—* wherein x is an integer number from 5 to 30).

Copolymers that can preferably be used as contemplated herein comprise at least one structural unit of the formula (a1-1), at least one structural unit of the formula (a1-2) and at least one structural unit of the formula (a2-1)

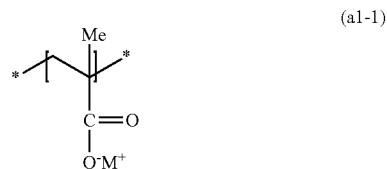

-continued

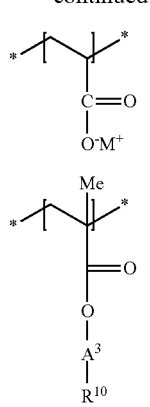

(a1-2)

(a2-1)

wherein
M+ is independently of one another a physiologically tolerable cation,
$R^{10}$ is a ($C_8$ to $C_{30}$) alkyl group (particularly octyl (capryl), decyl (caprinyl), dodecyl (lauryl), tetradecyl (myristyl), hexadecyl (cetyl), octadecyl (stearyl), eicosyl (arachyl) or docosyl (behenyl)) and
$A^3$ is a group *—$(CH_2CH_2O)_x$—*, wherein x is an integer number from 5 to 35, particularly from 15 to 30 (15, 16, 17, 18, 19, 20, 21, 22, 23, 24, 25, 26, 27, 28, 29, 30).

For clarity, it should be mentioned for a person not skilled in the art that according to formula (a2) or (a2-1) the radical $R^{10}$ always binds to the oxygen atom of group $A^3$.

Additionally preferably, those amphiphilic, anionic polymers (a) are to be used that are selected from copolymers of acrylic acid with methacrylic acid, at least one ($C_1$ to $C_4$) alkyl acrylate and at least one ethoxylated methacrylic ester and/or ethoxylated acrylic ester.

These copolymers (a) can be described by the formula (a-i)

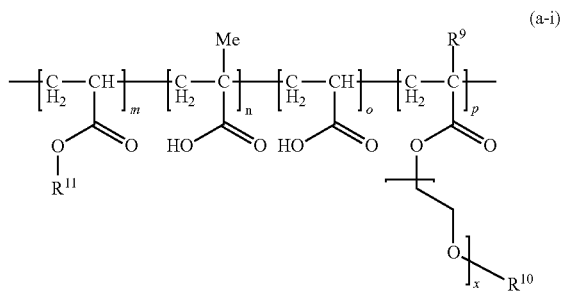

(a-i)

wherein
the indices m, n, o and p vary depending on the molar mass of the polymer,
$R^9$ is a hydrogen atom or a methyl group,
$R^{10}$ is a hydrocarbyl with 8 to 30, particularly with 10 to 24, carbon atoms
$R^{11}$ is a ($C_1$ to $C_4$) alkyl group (preferably —$CH_3$, —$CH_2CH_3$, —$CHMe_2$, —$CH_2CH_2CH_3$, —$CH_2CHMeCH_3$ or —$CH_2CH_2CH_2CH_3$, exceptionally preferably —$CH_3$ and/or —$CH_2CH_3$), x is 5 to 35 (particularly 15 to 30).

The arrangement of the structural units in the formula (a-i) above does not mean that the copolymers (a) are necessarily block copolymers. The structural units can rather more occur statistically distributed in the model.

Particularly preferable agents as contemplated herein are exemplified in that they as copolymer (a) contain copolymers of acrylic acid, methacrylic acid, ($C_1$ to $C_4$) alkyl acrylate, and ethoxylated (meth)acrylic esters with a molar mass of about 100 to about 500 kDa, preferably of about 150 to about 400 kDa, further preferably of about 200 to about 300 kDa and particularly of about 225 to about 275 kDa. The indices m, n, o and p according to the embodiment of the formula (a-i) correspond.

Particularly preferable copolymers (a) have about 20 to about 30 EO units (x=20, 21, 22, 23, 24, 25, 26, 27, 28, 29, 30) and have a behenyl radical as radical R.

An exceptionally preferable amphiphilic, anionic polymer (a) has 20 EO units and is esterified with stearyl alcohol. A corresponding acrylate copolymer (a) comprises at least one structural unit (a1) and at least one structural unit (a2),

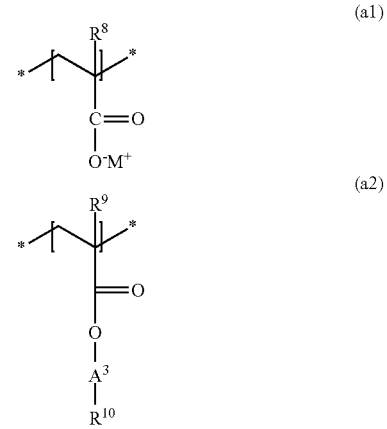

(a1)

(a2)

wherein
$R^8$ is a hydrogen atom or a methyl group,
$R^9$ is a methyl group
$R^{10}$ is an octadecyl group (stearyl group),
M+ is a physiologically tolerable cation and
$A^3$ is a group *—$(CH_2CH_2O)_x$—*, wherein x is an integer number from 20.

A polymer of this kind with the INCI designation acrylates/steareth-20 methacrylate copolymer is available, for instance, under the name Aculyn® 22 (Rahm & Haas). In the form available commercially this has a solids content of around from about 29.5 to about 30.5 wt. % and a pH value of from about 2.2 to about 3.2.

A further exceptionally preferable amphiphilic, anionic polymer (a) has 25 EO units and is esterified with behenyl alcohol. A corresponding acrylate copolymer (a) comprises at least one structural unit (a1) and at least one structural unit (a2),

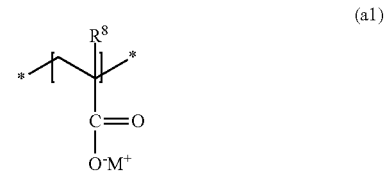

(a1)

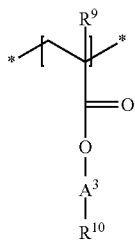

(a2)

wherein
$R^8$ is a hydrogen atom or a methyl group,
$R^9$ is a methyl group
$R^{10}$ is a docosyl group (behenyl group),
$M^+$ is a physiologically tolerable cation and
$A^3$ is a group *—$(CH_2CH_2O)_x$—*, wherein x is an integer number from 25.

A polymer of this kind with the INCI designation acrylates/beheneth-25 methacrylate copolymer is available, for instance, under the trade name Aculyn® 28 (Rahm & Haas). In the form available commercially this has a solids content of around from about 19 to about 21 wt. % and a pH value of from about 3.5 to about 4.0.

These amphiphilic, anionic polymers (a) can be cross-linked or uncross-linked. Preferred amphiphilic, anionic copolymers (a) are, however, not cross-linked.

"Cross-linked" "cross-linking" shall be understood for the purposes as contemplated herein to mean the linking of polymer chains together by covalent chemical bonding, with the formation of a network. This covalent linking of the polymer chains may be achieved by employing direct covalent bonding or by way of a molecule fragment bridging the polymer chains. The molecule fragment bonds to the polymer chains bridged by the molecule fragment by employing a covalent chemical bond in each case. For the purposes as contemplated herein, "uncross-linked" is to be understood to mean that no previously defined cross-linking is present.

Particularly preferable agents as contemplated herein are exemplified in that the amphiphilic, anionic polymers (a) have a molar mass of from about 100 to about 500 kDa, preferably of from about 150 to about 400 kDa, further preferably of from about 200 to from about 300 kDa and particularly of from about 225 to about 275 kDa.

The cosmetic compositions as contemplated herein contain as the second essential component an anionic acrylate copolymer (b).

The anionic acrylate copolymer (b) is built up of at least the following monomer units: at least one (meth)acrylic acid unit (b1), at least one (meth)acrylic acid ethyl ester unit (b2) and at least one (meth)acrylic acid ester unit (b3), which is different from the (meth)acrylic acid ethyl ester unit (b2) and a hydrophobic group as the ester group.

The copolymer (b) can, as contemplated herein, be built up from further monomer units. According to embodiments as contemplated herein, the copolymer (b) is, however, only built up from the units (b1), (b2) and (b3), i.e. it is of units derived from these monomer units.

The at least one (meth)acrylic acid unit (b1) can be a methacrylic acid or acrylic acid unit, wherein a methacrylic acid unit is preferable.

The at least one (meth)acrylic acid ethyl ester unit (b2) can be a methacrylic acid ethyl ester unit or an acrylic acid ethyl ester unit, wherein an acrylic acid ethyl ester unit is preferable.

The at least one (meth)acrylic acid ester unit (b3) can, as contemplated herein, be a (meth)acrylic acid alkyl ester unit. The alkyl group of the (meth)acrylic acid alkyl ester unit is used to control the hydrophobicity of the copolymer. The alkyl group is preferably a linear or branched alkyl group with 2 to 30 carbon atoms, preferably 3 to 12 carbon atoms. The hydrophobic group can, as contemplated herein, also be a hydrophobic group other than an alkyl group, e.g. an aromatic hydrocarbon ester group. An example might be a substituted or non-substituted phenyl ester group or a substituted or non-substituted alkylene phenyl ester group, e.g. a benzyl ester group.

The viscosity of the anionic acrylate copolymer (b) used in the cosmetic composition with a solids content of 2 wt. % and a neutralized solution at 25° C. is preferably no more than from about 60000 to about 120000 cPS.

Suitable anionic acrylate copolymers (b) are available commercially under the INCI designation acrylates copolymer (and) water. Most preferable is the anionic acrylate copolymer (b) AquaStyle® SH-100 polymer by Ashland, Inc. In the form available commercially this has a solids content of around from about 28 to about 32 wt. % and a pH value of from about 2.1 to about 4.0.

The cosmetic composition of the present disclosure contains the acrylate copolymer (a) and acrylate copolymer (b) in quantities usual and suitable for styling products, which can be adapted for the particular form.

The composition as contemplated herein can contain the copolymer (a) in a volume of from about 0.05 to about 5.0 wt. %, related to the total weight of the composition claimed, for example. Preferred are fractions of the copolymer (a) of from about 0.1 to about 4.0 wt. % and particularly of from about 0.2 to about 2.0 wt. %, each stated as a solids content of the active substance in the cosmetic composition.

The cosmetic composition as contemplated herein contains copolymer (b) in a fraction of from about 0.05 to about 5.0 wt. % for instance, related to the total weight of the cosmetic composition, preferably from about 0.5 to about 4.0 wt. %, further preferably from about 1.0 to about 3.0 wt. %, each stated as a solids content of the active substance in the cosmetic composition.

The cosmetic compositions claimed are exemplified over alternative cosmetic agents in particular by an improved long-term hold (curl retention) in addition to the advantages described above. A weight ratio of the polymers a) and b) in the cosmetic of from about 5:1 to about 1:5, preferably of from about 3:1 to about 1:3 and particularly of from about 2:1 to about 1:2 has proved particularly advantageous for the cosmetic characteristics of the agent claimed.

In a particularly preferable embodiment as contemplated herein, the cosmetic composition contains as the amphiphilic anionic acrylate copolymer (a) the copolymer available commercially under the designation Aculyn® 22 or the copolymer available commercially under the designation Aculyn® 28 and as the anionic acrylate copolymer (b) the copolymer available commercially under the designation AquaStyle® SH-100. Particularly good results in respect of a combination of stiffness and curl hold have been achieved with this combination. This polymer combination is particularly advantageous for styling products in gel form.

Further generally required characteristics of styling products, such as moisture resistance and low tack, for instance, are particularly also achieved with this combination, particularly when made up as hair gel.

The acrylate copolymers (a) and (b) are preferably used in the cosmetic composition in a partially neutralized or neutralized form. Preferably at least one alkanolamine is used for neutralization. The alkanolamines which may be used as alkalization agents as contemplated herein are preferably selected from primary amines with a C2-C5 alkyl parent, carrying at least one hydroxyl group. Particularly preferred alkanolamines are selected from the group which is formed from 2-aminoethane-1-ol (monoethanolamine), tris(2-hydroxyethyl)-amine (triethanolamine), 3-aminopropane-1-ol, 4-aminobutane-1-ol, 5-aminopentane-1-ol, 1-aminopropane-2-ol, 1-aminobutane-2-ol, 1-aminopentane-2-ol, 1-aminopentane-3-ol, 1-aminopentane-4-ol, 3-amino-2-methylpropane-1-ol, 1-amino-2-methylpropane-2-ol, 3-aminopropane-1,2-diol, 2-amino-2-methylpropane-1,3-diol. Alkanolamine exceptionally preferred as contemplated herein are selected from the group of 2-aminoethane-1-ol, 2-amino-2-methylpropane-1-ol and 2-amino-2-methyl-propane-1,3-diol. 2-amino-2-methyl propanol has proved to be a particularly suitable neutralization agent. As contemplated herein, preferred cosmetic agents thus contain 2-amino-2-methyl propanol. The 2-amino-2-methyl propanol is preferably used in the agents claimed in a quantity which does not exceed that quantity needed to neutralize the acrylate copolymers (a) and (b). Preferably, the quantities used in the compositions claimed of 2-amino-2-methyl propanol amount to from about 80 to about 100%, particularly preferably from about 90 to about 100% and particularly from about 95 to about 100% of the quantity required for the complete neutralization of the acrylate copolymers (a) and (b). In a preferable embodiment, the weight fraction of the 2-amino-2-methyl propanol is from about 0.05 to about 7.0 wt. %, preferably from about 0.1 to about 5.0 wt. % and particularly from about 0.1 to about 3.0 wt. % of the total weight of the cosmetic agent.

In summary, a preferred cosmetic composition for the temporary shaping of keratinous fibers contains, relative to its total weight:
(a) from about 0.2 to about 2.0 wt. % of at least one amphiphilic, anionic acrylate copolymer (a), comprising at least one structural unit of the formula (a1-1), at least one structural unit of the formula (a1-2) and at least one structural unit of the formula (a2-1)

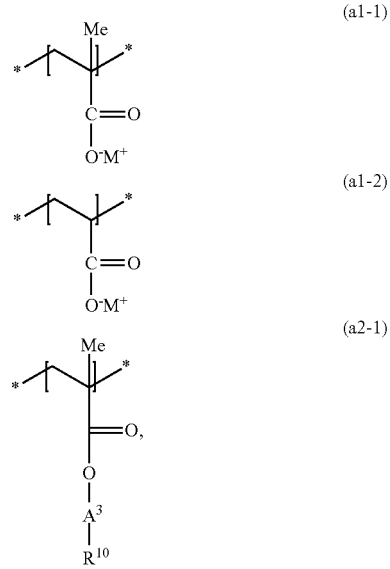

wherein
M⁺ is independently of one another a physiologically tolerable cation,
R¹⁰ is a (C₈ to C₃₀) alkyl group, and
A³ is a group *—(CH₂CH₂O)ₓ—*, wherein x is an integer number from 5 to 35, particularly from 15 to 30; and
(b) from about 0.5 to about 4.0 wt. % of at least one anionic copolymer (b), which is built up of at least the following monomer units:
(b1) at least one (meth)acrylic acid unit
(b2) at least one (meth)acrylic acid ethyl ester unit
(b3) at least one (meth)acrylic acid ester unit which is different from the (meth)acrylic acid ethyl ester unit (b2) and comprises a hydrophobic group as an ester group.

The cosmetic composition as contemplated herein preferably contains one or more further component(s) acting as thickening agents or gelling agents which is/are different from the acrylate copolymers (a) and (b) and likewise support(s) the formation of a film. Examples include cationic, anionic, non-ionic or amphoteric polymers. The weight fraction of these further components in the total weight of the cosmetic composition can be comparatively low because of the presence of the components (a) and (b) and is, for instance, from about 0.02 to about 3 wt. %, preferably from about 0.05 to about 1.5 wt. % and even more preferably from about 0.2 to about 0.8 wt. %.

Examples are acrylamide/ammonium acrylate copolymer, acrylamides/DMAPA acrylates/methoxy PEG methacrylate copolymer, acrylamidopropyltrimonium chloride/acrylamide copolymer, acrylamidopropyltrimonium chloride/acrylates copolymer, acrylates/acetoacetoxyethyl methacrylate copolymer, acrylates/acrylamide copolymer, acrylates/ammonium methacrylate copolymer, acrylates/t-butylacrylamide copolymer, acrylates/c1-2 succinates/hydroxyacrylates copolymer, acrylates/lauryl acrylate/stearyl acrylate/ethylamine oxide methacrylate copolymer, acrylates/octylacrylamide copolymer, acrylates/octylacrylamide/diphenyl amodimethicone copolymer, acrylates/stearyl acrylate/ethylamine oxide methacrylate copolymer, acrylates/VA copolymer, acrylates/VP copolymer, adipic acid/diethylenetriamine copolymer, adipic acid/dimethylaminohydroxypropyl diethylenetriamine copolymer, adipic acid/epoxypropyl diethylenetriamine copolymer, adipic acid/isophthalic acid/neopentyl glycol/trimethylolpropane copolymer, allyl stearate/VA copolymer, aminoethylacrylate phosphate/acrylates copolymer, aminoethylpropanediol-acrylates/acrylamide copolymer, aminoethylpropanediol-AMPD-acrylates/diacetoneacrylamide copolymer, ammonium VA/acrylates copolymer, AMPD-acrylates/diacetoneacrylamide copolymer, AMP-acrylates/allyl methacrylate copolymer, AMP-acrylates/C1-18 alkyl acrylates/C1-8 alkyl acrylamide copolymer, AMP-acrylates/diacetoneacrylamide copolymer, AMP-acrylates/dimethylaminoethylmethacrylate copolymer, bacillus/rice bran extract/soybean extract ferment filtrate, bis-butyloxyamodimethicone/PEG-60 copolymer, butyl acrylate/ethylhexyl methacrylate copolymer, butyl acrylate/hydroxypropyl dimethicone acrylate copolymer, butylated PVP, butyl ester of ethylene/MA copolymer, butyl ester of PVM/MA copolymer, calcium/sodium PVM/MA copolymer, corn starch/acrylamide/sodium acrylate copolymer, diethylene glycolamine/epichlorohydrin/piperazine copolymer, dimethicone crosspolymer, diphenyl amodimethicone, ethyl ester of PVM/MA copolymer, hydrolyzed wheat protein/PVP crosspolymer, isobutylene/ethylmaleimide/hydroxyethylmaleimide copolymer, isobutylene/MA copolymer, isobutylmethacrylate/bis-hydroxypropyl dimethicone acrylate copolymer, isopropyl ester of PVM/MA copolymer, lauryl acrylate crosspolymer, lauryl methacrylate/glycol dimethacrylate crosspolymer, MEA-sulfite, methacrylic acid/sodium acrylamidomethyl propane sulfonate copolymer, methacryloyl ethyl betaine/acrylates copolymer, octylacrylamide/acrylates/butylaminoethyl methacrylate copolymer, PEG/PPG-25/25 dimethicone/acrylates copolymer, PEG-8/SMDI copolymer, polyacrylamide, polyacrylate-6, polybeta-alanine/glutaric acid crosspolymer, polybutylene terephthalate, polyester-1, polyethylacrylate, polyethylene terephthalate, polymethacryloyl ethyl betaine, polypentaerythrityl terephthalate, polyperfluoroperhydrophenanthrene, polyquaternium-1, polyquaternium-2, polyquaternium-4, polyquaternium-5, polyquatemium-6, polyquaternium-7, polyquaternium-8, polyquatemium-9, polyquatemium-10, polyquatemium-11, polyquaternium-12, polyquaternium-13, polyquatemium-14, polyquatemium-15, polyquaternium-16, polyquaternium-17, polyquatemium-18, polyquatemium-19, polyquaternium-20, polyquaternium-22, polyquatemium-24, polyquaternium-27, polyquaternium-28, polyquaternium-29, polyquatemium-30, polyquatemium-31, polyquaternium-32, polyquaternium-33, polyquatemium-34, polyquatemium-35, polyquaternium-36, polyquaternium-37, polyquaternium-39, polyquatemium-45, polyquaternium-46, polyquaternium-47, polyquatemium-48, polyquatemium-49, polyquaternium-50, polyquaternium-55, polyquaternium-56, polysilicone-9, polyurethane-1, polyurethane-6, polyurethane-10, polyvinyl acetate, polyvinyl butyral, polyvinylcaprolactam, polyvinylformamide, polyvinyl imidazolinium acetate, polyvinyl methyl ether, potassium butyl ester of PVM/MA copolymer, potassium ethyl ester of PVM/MA copolymer, PPG-70 polyglyceryl-10 ether, PPG-12/SMDI copolymer, PPG-51/SMDI copolymer, PPG-10 sorbitol, PVM/MA copolymer, PVP, PVP/VA/itaconic acid copolymer, PVP/VA/vinyl propionate copolymer, rhizobian gum, rosin acrylate, shellac, sodium butyl ester of PVM/MA copolymer, sodium ethyl ester of PVM/MA copolymer, sodium polyacrylate, sterculia urens gum, terephthalic acid/isophthalic acid/sodium isophthalic acid sulfonate/glycol copolymer, trimethylolpropane triacrylate, trimethylsiloxysilylcarbamoyl pullulan, VA/crotonates copolymer, VA/crotonates/methacryloxybenzophenone-1 copolymer, VA/crotonates/vinyl neodecanoate copolymer, VA/crotonates/vinyl propionate copolymer, VA/DBM copolymer, VA/vinyl butyl benzoate/crotonates copolymer, vinylamine/vinyl alcohol copolymer, vinyl caprolactam/VP/dimethylaminoethyl methacrylate copolymer, VP/acrylates/lauryl methacrylate copolymer, VP/dimethylaminoethylmethacrylate copolymer, VP/DMAPA acrylates copolymer, VP/hexadecene copolymer, VP/VA copolymer, VP/vinyl caprolactam/dmapa acrylates copolymer, yeast palmitate and styrene/VP copolymer.

Examples of non-ionic polymers are:

Vinylpyrrolidone/vinylester copolymers, as are commercially distributed under the trademark Luviskol (BASF) for instance. Luviskol VA 64 and Luviskol VA 73, each vinylpyrrolidone/vinyl acetate copolymers, are preferred non-ionic polymers.

Cellulose ethers, such as hydroxypropyl cellulose, hydroxyethyl cellulose and methyl hydroxypropyl cellulose, as are distributed commercially under the trademarks Culminal and Benecel (AQUALON), for instance.

shellac.

Polyvinylpyrrolidones, as are commercially distributed under the name Luviskol (BASF) for instance.

Siloxanes. These siloxanes can be both water-soluble and water-insoluble. Both volatile and non-volatile siloxanes are suitable, wherein those compounds the boiling point of which at atmospheric pressure is above 200° C. are considered to be non-volatile siloxanes.

Preferred siloxanes are polydialkylsiloxanes, such as polydimethylsiloxane, for example, polyalkylarylsiloxanes, such as polyphenylmethylsiloxane, for example, ethoxylated polydialkylsiloxanes and polydialkylsiloxane, which contain amine and/or hydroxy groups.

Glycosidically substituted silicones.

Preferred as the further component acting as a gelling agent is a homopolyacrylic acid (INCI: carbomer), which is available commercially in various forms under the name Carbopol®. The carbomer is preferably contained in a fraction of from about 0.02 to about 3 wt. %, preferably from about 0.05 to about 1.5 wt. % and even more preferably from about 0.2 to about 0.8 wt. %, related to the total weight of the cosmetic composition.

The film-forming polymers preferably used as contemplated herein because of their cosmetic effect in combination with copolymers a) and b) are, in particular, the polyvinylpyrrolidones (INCI designation: PVP) and the vinylpyrrolidone/vinyl acetate copolymers (INCI designation VP/VA copolymer), wherein the fraction by weight of these polymers is preferably restricted to quantities between from about 1.0 and about 10 wt. %. Especially preferable cosmetic compositions as contemplated herein are therefore exemplified in that they further contain from about 1.0 to about 10 wt. % related to their total weight of polyvinylpyrrolidone and/or vinylpyrrolidone/vinyl acetate copolymers, preferably polyvinylpyrrolidone. Particularly preferred cosmetic agents have a weight fraction of the polyvinylpyrrolidone and/or vinylpyrrolidone/vinyl acetate copolymer c) of the total weight of the cosmetic agent of from about 2.0 to about 8.5 wt. %, preferably from about 3.0 to about 7.0 wt. %.

The cosmetic composition claimed can contain further materials usually found in styling products. Additional care ingredients may be mentioned as further suitable adjuvants and additives.

The agent can contain, for example, at least one protein hydrolysate and/or one of its derivatives as the care ingredient. Protein hydrolysates are product mixtures obtained by the acidic, basic or enzyme catalyzed breakdown of proteins. The concept of protein hydrolysates is also understood as contemplated herein to include total hydrolysates and individual amino acids and their derivatives as well as mixtures of various amino acids. The molar mass of the protein hydrolysates which may be used as contemplated herein lies between about 75, the molar mass of glycine, and about 200,000, the molar mass is preferably from about 75 to about 50,000 and particularly preferably from about 75 to about 20,000 daltons.

The agent claimed can further contain at least one vitamin, a provitamin, a vitamin precursor and/or one of the derivatives thereof as the care ingredient. As contemplated herein, those vitamins, provitamins and vitamin precursor are preferably those that are usually assigned to the groups A, B, C, E, F and H.

The addition of panthenol, just like the addition of glycerine and/or propylene glycol, increases the flexibility of the polymer film formed on application of the agent claimed.

The agents as contemplated herein can further contain as a care ingredient at least one plant extract, and also monosaccharides or oligosaccharides and/or lipids.

Oil bodies are furthermore suited as a care ingredient. Vegetable oils, liquid paraffin oils, isoparaffin oils and synthetic hydrocarbons, and also di-n-alkyl ether with a total of between 12 to 36 C atoms, particularly 12 to 24 C atoms, can be numbered among the natural and synthetic cosmetic oil bodies. Preferred cosmetic agents as contemplated herein contain at least one oil body, preferably at least an oil body from the group of silicone oils. The group of silicone oils includes in particular the dimethicones, in which the cyclomethicones are also counted, the amino functional silicones and the dimethiconols. The dimethicones can be both linear and branched, and also cyclical or cyclical and branched. Suitable silicone oils or silicone gums are, in particular, dialkyl siloxanes and alkylaryl siloxanes, such as dimethyl polysiloxane and methylphenyl polysiloxane, for instance, and their alkoxylated, quaternized or even anionic derivatives. Cyclic and linear polydialkyl siloxanes, the alkoxylated and/or aminized derivatives thereof, dihydroxy polydimethylsiloxanes and poly phenyl alkyl siloxanes are preferred.

Ester oils, that is to say esters of 6-C30 fatty acids with C2-C30 fatty alcohols, preferably monoesters of the fatty acids with alcohols having 2 to 24 C atoms such as, for instance, isopropyl myristate (Rilanit® 1 PM), isononanoic acid-C16-18-alkyl ester (Cetiol® SN), 2-ethylhexyl palmitate (Cegesoft® 24), stearic acid-2-ethylhexyl ester (Cetiol® 868), cetyl oleate, glyceryl tricaprylate, coconut oil alcohol caprinate/caprylate (Cetiol® LC), n-butyl stearate, oleyl erucate (Cetiol® J 600), isopropyl palmitate (Rilanit® IPP), oleyl oleate (Cetiol®), lauric acid hexyl ester (Cetiol® A), di-n-butyl adipate (Cetiol® B), myristyl myristate (Cetiol® MM), cetearyl isononanoate (Cetiol® SN), oleic acid decyl ester (Cetiol® V) are further preferred care oil bodies.

Furthermore, suited as care ingredients are dicarboxylic acid, symmetrical, unsymmetrical or cyclic esters of carbonic acid with fatty alcohols, tri-fatty acid esters of saturated and/or unsaturated linear and/or branched fatty acids with glycerine or fatty acid partial glycerides, which is understood as monoglycerides, diglycerides and their technical mixtures.

Furthermore emulsifiers or surfactants are preferably included in the composition claimed. PEG derivatives of hydrogenated castor oil, which is available under the name PEG hydrogenated castor oil, for instance, e.g. PEG-30 hydrogenated castor oil, PEG-33 hydrogenated castor oil, PEG-35 hydrogenated castor oil, PEG-36 hydrogenated castor oil or PEG-40 hydrogenated castor oil. The use of PEG-40 hydrogenated castor oil is preferred as contemplated herein. These are preferably contained in a quantity of from about 0.05 to about 1.5 wt. %, more preferably from about 0.1 to about 1.0 wt. %, likewise preferably from about 0.2 to about 0.8 wt. % or from about 0.3 to about 0.6 wt. %.

The cosmetic agents claimed contain the ingredients or active substances in a cosmetically acceptable base.

Preferred cosmetically acceptable bases are aqueous, alcoholic or aqueous/alcoholic media with preferably at least 10 wt. % water, calculated in relation to the total weight of the agent.

Particularly preferably the cosmetic base contains water, particularly in the volume such that the cosmetic agent, calculated in relation to the total weight of the agent, contains at least about 10 wt. %, particularly at least about 20.0 wt. %, most preferably at least about 40 wt. % water. Quite particularly preferably, cosmetic agents comprise, relative to their total weight, a water fraction between from about 50 and about 95 wt. %, preferably between from about 60 and about 90 wt. % and particularly between from about 65 and about 85 wt. %.

The short-chain alcohols with 1 to 4 carbon atoms, such as ethanol and isopropyl alcohol, routinely used for cosmetic purposes can, in particular, be included as the alcohols.

Glycerine and/or ethylene glycol and/or 1,2-propylene glycol in a quantity from about 0 to about 30 wt. % relative to the full agent are examples of water-soluble solvents as cosolvents.

Tabular Overview

The composition of some preferred cosmetic agents can be found in the tables below (specifications in wt. % relative to the total weight of the cosmetic agent unless otherwise stated).

|  | Formula 1 | Formula 2 | Formula 3 | Formula 4 | Formula 5 |
|---|---|---|---|---|---|
| Copolymer a) | 0.05 to 5.0 | 0.1 to 4.0 | 0.1 to 4.0 | 0.2 to 2.0 | 0.2 to 2.0 |
| Copolymer b) | 0.05 to 5.0 | 0.05 to 5.0 | 0.5 to 4.0 | 0.5 to 4.0 | 1.0 to 3.0 |
| Misc | add 100 | add 100 | add 100 | add 100 | add 100 |

|  | Formula 1a | Formula 2a | Formula 3a | Formula 4a | Formula 5a |
|---|---|---|---|---|---|
| Copolymer a): Aculyn® 22 (stated as solids content) | 0.05 to 5.0 | 0.1 to 4.0 | 0.1 to 4.0 | 0.2 to 2.0 | 0.2 to 2.0 |
| Copolymer b): AquaStyle® SH-100 (stated as solids content) | 0.05 to 5.0 | 0.05 to 5.0 | 0.5 to 4.0 | 0.5 to 4.0 | 1.0 to 3.0 |
| Misc | add 100 | add 100 | add 100 | add 100 | add 100 |

|  | Formula 1b | Formula 2b | Formula 3b | Formula 4b | Formula 5b |
|---|---|---|---|---|---|
| Copolymer a): Aculyn® 28 ☐ (stated as solids content) | 0.05 to 5.0 | 0.1 to 4.0 | 0.1 to 4.0 | 0.2 to 2.0 | 0.2 to 2.0 |
| Copolymer b): AquaStyle® SH-100 (stated as solids content) | 0.05 to 5.0 | 0.05 to 5.0 | 0.5 to 4.0 | 0.5 to 4.0 | 1.0 to 3.0 |
| Misc | add 100 | add 100 | add 100 | add 100 | add 100 |

|  | Formula 6 | Formula 7 | Formula 8 | Formula 9 | Formula 10 |
|---|---|---|---|---|---|
| Copolymer a) | 0.05 to 5.0 | 0.1 to 4.0 | 0.1 to 4.0 | 0.2 to 2.0 | 0.2 to 2.0 |
| Copolymer b) | 0.05 to 5.0 | 0.05 to 5.0 | 0.5 to 4.0 | 0.5 to 4.0 | 1.0 to 3.0 |
| Polyvinylpyrrolidone | 1.0 to 10 | 2.0 to 8.5 | 2.0 to 8.5 | 3.0 to 7.0 | 3.0 to 7.0 |
| Misc | add 100 | add 100 | add 100 | add 100 | add 100 |

-continued

|  | Formula 6a | Formula 7a | Formula 8a | Formula 9a | Formula 10a |
|---|---|---|---|---|---|
| Copolymer a): Aculyn ® 22 (stated as solids content) | 0.05 to 5.0 | 0.1 to 4.0 | 0.1 to 4.0 | 0.2 to 2.0 | 0.2 to 2.0 |
| Copolymer b): AquaStyle ® SH-100 (stated as solids content) | 0.05 to 5.0 | 0.05 to 5.0 | 0.5 to 4.0 | 0.5 to 4.0 | 1.0 to 3.0 |
| Polyvinylpyrrolidone | 1.0 to 10 | 2.0 to 8.5 | 2.0 to 8.5 | 3.0 to 7.0 | 3.0 to 7.0 |
| Misc | add 100 | add 100 | add 100 | add 100 | add 100 |

|  | Formula 6b | Formula 7b | Formula 8b | Formula 9b | Formula 10b |
|---|---|---|---|---|---|
| Copolymer a): Aculyn ® 28 (stated as solids content) | 0.05 to 5.0 | 0.1 to 4.0 | 0.1 to 4.0 | 0.2 to 2.0 | 0.2 to 2.0 |
| Copolymer b): AquaStyle ® SH-100 (stated as solids content) | 0.05 to 5.0 | 0.05 to 5.0 | 0.5 to 4.0 | 0.5 to 4.0 | 1.0 to 3.0 |
| Polyvinylpyrrolidone | 1.0 to 10 | 2.0 to 8.5 | 2.0 to 8.5 | 3.0 to 7.0 | 3.0 to 7.0 |
| Misc | add 100 | add 100 | add 100 | add 100 | add 100 |

|  | Formula 11 | Formula 12 | Formula 13 | Formula 14 | Formula 15 |
|---|---|---|---|---|---|
| Copolymer a) | 0.05 to 5.0 | 0.1 to 4.0 | 0.1 to 4.0 | 0.2 to 2.0 | 0.2 to 2.0 |
| Copolymer b) | 0.05 to 5.0 | 0.05 to 5.0 | 0.5 to 4.0 | 0.5 to 4.0 | 1.0 to 3.0 |
| Vinylpyrrolidone/vinyl acetate | 1.0 to 10 | 2.0 to 8.5 | 2.0 to 8.5 | 3.0 to 7.0 | 3.0 to 7.0 |
| Misc | add 100 | add 100 | add 100 | add 100 | add 100 |

|  | Formula 11a | Formula 12a | Formula 13a | Formula 14a | Formula 15a |
|---|---|---|---|---|---|
| Copolymer a): Aculyn ® 22 (stated as solids content) | 0.05 to 5.0 | 0.1 to 4.0 | 0.1 to 4.0 | 0.2 to 2.0 | 0.2 to 2.0 |
| Copolymer b): AquaStyle ® SH-100 (stated as solids content) | 0.05 to 5.0 | 0.05 to 5.0 | 0.5 to 4.0 | 0.5 to 4.0 | 1.0 to 3.0 |
| Vinylpyrrolidone/vinyl acetate | 1.0 to 10 | 2.0 to 8.5 | 2.0 to 8.5 | 3.0 to 7.0 | 3.0 to 7.0 |
| Misc | add 100 | add 100 | add 100 | add 100 | add 100 |

|  | Formula 11b | Formula 12b | Formula 13b | Formula 14b | Formula 15b |
|---|---|---|---|---|---|
| Copolymer a): Aculyn ® 28 (stated as solids content) | 0.05 to 5.0 | 0.1 to 4.0 | 0.1 to 4.0 | 0.2 to 2.0 | 0.2 to 2.0 |
| Copolymer b): AquaStyle ® SH-100 (stated as solids content) | 0.05 to 5.0 | 0.05 to 5.0 | 0.5 to 4.0 | 0.5 to 4.0 | 1.0 to 3.0 |
| Vinylpyrrolidone/vinyl acetate | 1.0 to 10 | 2.0 to 8.5 | 2.0 to 8.5 | 3.0 to 7.0 | 3.0 to 7.0 |
| Misc | add 100 | add 100 | add 100 | add 100 | add 100 |

|  | Formula 16 | Formula 17 | Formula 18 | Formula 19 | Formula 20 |
|---|---|---|---|---|---|
| Copolymer a) | 0.05 to 5.0 | 0.1 to 4.0 | 0.1 to 4.0 | 0.2 to 2.0 | 0.2 to 2.0 |
| Copolymer b) | 0.05 to 5.0 | 0.05 to 5.0 | 0.5 to 4.0 | 0.5 to 4.0 | 1.0 to 3.0 |
| Carbomer | 0.02 to 3.0 | 0.05 to 2.0 | 0.05 to 1.5 | 0.2 to 1.0 | 0.4 to 0.8 |
| Misc | add 100 | add 100 | add 100 | add 100 | add 100 |

|  | Formula 16a | Formula 17a | Formula 18a | Formula 19a | Formula 20a |
|---|---|---|---|---|---|
| Copolymer a): Aculyn ® 22 (stated as solids content) | 0.05 to 5.0 | 0.1 to 4.0 | 0.1 to 4.0 | 0.2 to 2.0 | 0.2 to 2.0 |
| Copolymer b): AquaStyle ® SH-100 (stated as solids content) | 0.05 to 5.0 | 0.05 to 5.0 | 0.5 to 4.0 | 0.5 to 4.0 | 1.0 to 3.0 |
| Carbomer | 0.02 to 3.0 | 0.05 to 2.0 | 0.05 to 1.5 | 0.2 to 1.0 | 0.4 to 0.8 |
| Misc | add 100 | add 100 | add 100 | add 100 | add 100 |

|  | Formula 16b | Formula 17b | Formula 18b | Formula 19b | Formula 20b |
|---|---|---|---|---|---|
| Copolymer a): Aculyn ® 28 (stated as solids content) | 0.05 to 5.0 | 0.1 to 4.0 | 0.1 to 4.0 | 0.2 to 2.0 | 0.2 to 2.0 |

-continued

|  |  |  |  |  |  |
|---|---|---|---|---|---|
| Copolymer b): AquaStyle ® SH-100 (stated as solids content) | 0.05 to 5.0 | 0.05 to 5.0 | 0.5 to 4.0 | 0.5 to 4.0 | 1.0 to 3.0 |
| Carbomer | 0.02 to 3.0 | 0.05 to 2.0 | 0.05 to 1.5 | 0.2 to 1.0 | 0.4 to 0.8 |
| Misc | add 100 | add 100 | add 100 | add 100 | add 100 |

|  | Formula 21 | Formula 22 | Formula 23 | Formula 24 | Formula 25 |
|---|---|---|---|---|---|
| Copolymer a) | 0.05 to 5.0 | 0.1 to 4.0 | 0.1 to 4.0 | 0.2 to 2.0 | 0.2 to 2.0 |
| Copolymer b) | 0.05 to 5.0 | 0.05 to 5.0 | 0.5 to 4.0 | 0.5 to 4.0 | 1.0 to 3.0 |
| PEG-40 hydrogenated castor oil | 0.05 to 1.5 | 0.1 to 1.0 | 0.2 to 0.9 | 0.3 to 0.8 | 0.4 to 0.6 |
| Misc | add 100 | add 100 | add 100 | add 100 | add 100 |

|  | Formula 21a | Formula 22a | Formula 23a | Formula 24a | Formula 25a |
|---|---|---|---|---|---|
| Copolymer a): Aculyn ® 22 (stated as solids content) | 0.05 to 5.0 | 0.1 to 4.0 | 0.1 to 4.0 | 0.2 to 2.0 | 0.2 to 2.0 |
| Copolymer b): AquaStyle ® SH-100 (stated as solids content) | 0.05 to 5.0 | 0.05 to 5.0 | 0.5 to 4.0 | 0.5 to 4.0 | 1.0 to 3.0 |
| PEG-40 hydrogenated castor oil | 0.05 to 1.5 | 0.1 to 1.0 | 0.2 to 0.9 | 0.3 to 0.8 | 0.4 to 0.6 |
| Misc | add 100 | add 100 | add 100 | add 100 | add 100 |

|  | Formula 21b | Formula 22b | Formula 23b | Formula 24b | Formula 25b |
|---|---|---|---|---|---|
| Copolymer a): Aculyn ® 28 (stated as solids content) | 0.05 to 5.0 | 0.1 to 4.0 | 0.1 to 4.0 | 0.2 to 2.0 | 0.2 to 2.0 |
| Copolymer b): AquaStyle ® SH-100 (stated as solids content) | 0.05 to 5.0 | 0.05 to 5.0 | 0.5 to 4.0 | 0.5 to 4.0 | 1.0 to 3.0 |
| PEG-40 hydrogenated castor oil | 0.05 to 1.5 | 0.1 to 1.0 | 0.2 to 0.9 | 0.3 to 0.8 | 0.4 to 0.6 |
| Misc | add 100 | add 100 | add 100 | add 100 | add 100 |

|  | Formula 26 | Formula 27 | Formula 28 | Formula 29 | Formula 30 |
|---|---|---|---|---|---|
| Copolymer a) | 0.05 to 5.0 | 0.1 to 4.0 | 0.1 to 4.0 | 0.2 to 2.0 | 0.2 to 2.0 |
| Copolymer b) | 0.05 to 5.0 | 0.05 to 5.0 | 0.5 to 4.0 | 0.5 to 4.0 | 1.0 to 3.0 |
| Water | 50 to 95 | 50 to 95 | 60 to 90 | 60 to 90 | 65 to 85 |
| Misc | add 100 | add 100 | add 100 | add 100 | add 100 |

|  | Formula 26a | Formula 27a | Formula 28a | Formula 29a | Formula 30a |
|---|---|---|---|---|---|
| Copolymer a): Aculyn ® 22 (stated as solids content) | 0.05 to 5.0 | 0.1 to 4.0 | 0.1 to 4.0 | 0.2 to 2.0 | 0.2 to 2.0 |
| Copolymer b): AquaStyle ® SH-100 (stated as solids content) | 0.05 to 5.0 | 0.05 to 5.0 | 0.5 to 4.0 | 0.5 to 4.0 | 1.0 to 3.0 |
| Water | 50 to 95 | 50 to 95 | 60 to 90 | 60 to 90 | 65 to 85 |
| Misc | add 100 | add 100 | add 100 | add 100 | add 100 |

|  | Formula 26b | Formula 27b | Formula 28b | Formula 29b | Formula 30b |
|---|---|---|---|---|---|
| Copolymer a): Aculyn ® 28 (stated as solids content) | 0.05 to 5.0 | 0.1 to 4.0 | 0.1 to 4.0 | 0.2 to 2.0 | 0.2 to 2.0 |
| Copolymer b): AquaStyle ® SH-100 (stated as solids content) | 0.05 to 5.0 | 0.05 to 5.0 | 0.5 to 4.0 | 0.5 to 4.0 | 1.0 to 3.0 |
| Water | 50 to 95 | 50 to 95 | 60 to 90 | 60 to 90 | 65 to 85 |
| Misc | add 100 | add 100 | add 100 | add 100 | add 100 |

|  | Formula 31 | Formula 32 | Formula 33 | Formula 34 | Formula 35 |
|---|---|---|---|---|---|
| Copolymer a) | 0.05 to 5.0 | 0.1 to 4.0 | 0.1 to 4.0 | 0.2 to 2.0 | 0.2 to 2.0 |
| Copolymer b) | 0.05 to 5.0 | 0.05 to 5.0 | 0.5 to 4.0 | 0.5 to 4.0 | 1.0 to 3.0 |
| Polyvinylpyrrolidone | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | add 100 | add 100 | add 100 | add 100 | add 100 |

|  | Formula 31a | Formula 32a | Formula 33a | Formula 34a | Formula 35a |
|---|---|---|---|---|---|
| Copolymer a): Aculyn ® 22 (stated as solids content) | 0.05 to 5.0 | 0.1 to 4.0 | 0.1 to 4.0 | 0.2 to 2.0 | 0.2 to 2.0 |
| Copolymer b): AquaStyle ® SH-100 (stated as solids content) | 0.05 to 5.0 | 0.05 to 5.0 | 0.5 to 4.0 | 0.5 to 4.0 | 1.0 to 3.0 |
| Polyvinylpyrrolidone | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | add 100 | add 100 | add 100 | add 100 | add 100 |

|  | Formula 31b | Formula 32b | Formula 33b | Formula 34b | Formula 35b |
|---|---|---|---|---|---|
| Copolymer a): Aculyn ® 28 (stated as solids content) | 0.05 to 5.0 | 0.1 to 4.0 | 0.1 to 4.0 | 0.2 to 2.0 | 0.2 to 2.0 |
| Copolymer b): AquaStyle ® SH-100 (stated as solids content) | 0.05 to 5.0 | 0.05 to 5.0 | 0.5 to 4.0 | 0.5 to 4.0 | 1.0 to 3.0 |
| Polyvinylpyrrolidone | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | add 100 | add 100 | add 100 | add 100 | add 100 |

|  | Formula 36 | Formula 37 | Formula 38 | Formula 39 | Formula 40 |
|---|---|---|---|---|---|
| Copolymer a) | 0.05 to 5.0 | 0.1 to 4.0 | 0.1 to 4.0 | 0.2 to 2.0 | 0.2 to 2.0 |
| Copolymer b) | 0.05 to 5.0 | 0.05 to 5.0 | 0.5 to 4.0 | 0.5 to 4.0 | 1.0 to 3.0 |
| Vinylpyrrolidone/vinyl acetate | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | add 100 | add 100 | add 100 | add 100 | add 100 |

|  | Formula 36a | Formula 37a | Formula 38a | Formula 39a | Formula 40a |
|---|---|---|---|---|---|
| Copolymer a): Aculyn ® 22 (stated as solids content) | 0.05 to 5.0 | 0.1 to 4.0 | 0.1 to 4.0 | 0.2 to 2.0 | 0.2 to 2.0 |
| Copolymer b): AquaStyle ® SH-100 (stated as solids content) | 0.05 to 5.0 | 0.05 to 5.0 | 0.5 to 4.0 | 0.5 to 4.0 | 1.0 to 3.0 |
| Vinylpyrrolidone/vinyl acetate | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | add 100 | add 100 | add 100 | add 100 | add 100 |

|  | Formula 36b | Formula 37b | Formula 38b | Formula 39b | Formula 40b |
|---|---|---|---|---|---|
| Copolymer a): Aculyn ® 28 (stated as solids content) | 0.05 to 5.0 | 0.1 to 4.0 | 0.1 to 4.0 | 0.2 to 2.0 | 0.2 to 2.0 |
| Copolymer b): AquaStyle ® SH-100 (stated as solids content) | 0.05 to 5.0 | 0.05 to 5.0 | 0.5 to 4.0 | 0.5 to 4.0 | 1.0 to 3.0 |
| Vinylpyrrolidone/vinyl acetate | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | add 100 | add 100 | add 100 | add 100 | add 100 |

|  | Formula 41 | Formula 42 | Formula 43 | Formula 44 | Formula 45 |
|---|---|---|---|---|---|
| Copolymer a) | 0.05 to 5.0 | 0.1 to 4.0 | 0.1 to 4.0 | 0.2 to 2.0 | 0.2 to 2.0 |
| Copolymer b) | 0.05 to 5.0 | 0.05 to 5.0 | 0.5 to 4.0 | 0.5 to 4.0 | 1.0 to 3.0 |
| Carbomer | 0.02 to 3.0 | 0.05 to 2.0 | 0.05 to 1.5 | 0.2 to 1.0 | 0.4 to 0.8 |
| Water | 50 to 95 | 50 to 95 | 60 to 90 | 60 to 90 | 65 to 85 |
| Misc | add 100 | add 100 | add 100 | add 100 | add 100 |

|  | Formula 41a | Formula 42a | Formula 43a | Formula 44a | Formula 45a |
|---|---|---|---|---|---|
| Copolymer a): Aculyn ® 22 (stated as solids content) | 0.05 to 5.0 | 0.1 to 4.0 | 0.1 to 4.0 | 0.2 to 2.0 | 0.2 to 2.0 |
| Copolymer b): AquaStyle ® SH-100 (stated as solids content) | 0.05 to 5.0 | 0.05 to 5.0 | 0.5 to 4.0 | 0.5 to 4.0 | 1.0 to 3.0 |
| Carbomer | 0.02 to 3.0 | 0.05 to 2.0 | 0.05 to 1.5 | 0.2 to 1.0 | 0.4 to 0.8 |
| Water | 50 to 95 | 50 to 95 | 60 to 90 | 60 to 90 | 65 to 85 |
| Misc | add 100 | add 100 | add 100 | add 100 | add 100 |

|  | Formula 41b | Formula 42b | Formula 43b | Formula 44b | Formula 45b |
|---|---|---|---|---|---|
| Copolymer a): Aculyn ® 28 (stated as solids content) | 0.05 to 5.0 | 0.1 to 4.0 | 0.1 to 4.0 | 0.2 to 2.0 | 0.2 to 2.0 |
| Copolymer b): AquaStyle ® SH-100 (stated as solids content) | 0.05 to 5.0 | 0.05 to 5.0 | 0.5 to 4.0 | 0.5 to 4.0 | 1.0 to 3.0 |
| Carbomer | 0.02 to 3.0 | 0.05 to 2.0 | 0.05 to 1.5 | 0.2 to 1.0 | 0.4 to 0.8 |
| Water | 50 to 95 | 50 to 95 | 60 to 90 | 60 to 90 | 65 to 85 |
| Misc | add 100 | add 100 | add 100 | add 100 | add 100 |

|  | Formula 46 | Formula 47 | Formula 48 | Formula 49 | Formula 50 |
|---|---|---|---|---|---|
| Copolymer a) | 0.05 to 5.0 | 0.1 to 4.0 | 0.1 to 4.0 | 0.2 to 2.0 | 0.2 to 2.0 |
| Copolymer b) | 0.05 to 5.0 | 0.05 to 5.0 | 0.5 to 4.0 | 0.5 to 4.0 | 1.0 to 3.0 |
| PEG-40 hydrogenated castor oil | 0.05 to 1.5 | 0.1 to 1.0 | 0.2 to 0.9 | 0.3 to 0.8 | 0.4 to 0.6 |
| Water | 50 to 95 | 50 to 95 | 60 to 90 | 60 to 90 | 65 to 85 |
| Misc | add 100 | add 100 | add 100 | add 100 | add 100 |

|  | Formula 46a | Formula 47a | Formula 48a | Formula 49a | Formula 50a |
|---|---|---|---|---|---|
| Copolymer a): Aculyn ® 22 (stated as solids content) | 0.05 to 5.0 | 0.1 to 4.0 | 0.1 to 4.0 | 0.2 to 2.0 | 0.2 to 2.0 |
| Copolymer b): AquaStyle ® SH-100 (stated as solids content) | 0.05 to 5.0 | 0.05 to 5.0 | 0.5 to 4.0 | 0.5 to 4.0 | 1.0 to 3.0 |
| PEG-40 hydrogenated castor oil | 0.05 to 1.5 | 0.1 to 1.0 | 0.2 to 0.9 | 0.3 to 0.8 | 0.4 to 0.6 |
| Water | 50 to 95 | 50 to 95 | 60 to 90 | 60 to 90 | 65 to 85 |
| Misc | add 100 | add 100 | add 100 | add 100 | add 100 |

|  | Formula 46b | Formula 47b | Formula 48b | Formula 49b | Formula 50b |
|---|---|---|---|---|---|
| Copolymer a): Aculyn ® 28 (stated as solids content) | 0.05 to 5.0 | 0.1 to 4.0 | 0.1 to 4.0 | 0.2 to 2.0 | 0.2 to 2.0 |
| Copolymer b): AquaStyle ® SH-100 (stated as solids content) | 0.05 to 5.0 | 0.05 to 5.0 | 0.5 to 4.0 | 0.5 to 4.0 | 1.0 to 3.0 |
| PEG-40 hydrogenated castor oil | 0.05 to 1.5 | 0.1 to 1.0 | 0.2 to 0.9 | 0.3 to 0.8 | 0.4 to 0.6 |
| Water | 50 to 95 | 50 to 95 | 60 to 90 | 60 to 90 | 65 to 85 |
| Misc | add 100 | add 100 | add 100 | add 100 | add 100 |

"Misc" is to be understood, for the purposes of this disclosure, to mean a cosmetic base, particularly (unless separately listed) water and, where appropriate, other conventional components of styling products.

The cosmetic composition of the present disclosure can be made up into the usual forms for the temporary shaping of hair, e.g. hair gel, hair spray, hair mousse or hair wax. It is preferably made up as hair gel.

Both hair mousses and hair sprays require the presence of expanding agents. As contemplated herein, however, preferably no or only small quantities of hydrocarbons should be used for this purpose. Propane, propane/butane mixtures and dimethyl ethers are, as contemplated herein, particularly suited as expanding agents.

The present disclosure also concerns the use of cosmetic compositions as contemplated herein for temporarily shaping keratinous fibers, particularly human hair, and a method for temporarily shaping keratinous fibers, particularly human hair, in which the cosmetic composition according the invention is applied to keratinous fibers.

A further subject matter of this patent application is the use of a cosmetic composition as contemplated herein for improving the moisture resistance of temporarily shaped keratinous fibers.

EXAMPLES

Example 1: The Following Hair Gels were Produced

| Component/raw material | INCI designation or chemical name | V1 | V2 | E1 |
|---|---|---|---|---|
| Aculyn ® 22[1] | Acrylates/steareth-20 copolymer methacrylate | 3.3 | — | 1.65 |

-continued

| Component/raw material | INCI designation or chemical name | V1 | V2 | E1 |
|---|---|---|---|---|
| AquaStyle SH-100[2] | Acrylates copolymer (and) water | — | 3.3 | 1.65 |
| AMP-ULTRA PC 2000 | Aminomethyl propanol | 0.34 | 0.3 | 0.32 |
| Water | | 96.36 | 96.4 | 96.38 |
| Total | | 100 | 100 | 100 |

[1] 30 wt. % active substance in water
[2] 30 wt. % active substance in water

The quantities are stated in the table as wt. % of the raw material concerned, related to the total composition. The polymer content in each of the compositions V1, V2 and E1 was 1.0 wt. %.

An HHCR test (High Humidity Curl Retention-Test: 6 hours) was performed on new Kerling hair strands to determine moisture resistance for the styling agents obtained (average value of determination on 5 hair strands each):

| | V1 | V2 | E1 |
|---|---|---|---|
| HHCR | 43% | 51% | 78% |

The polymer combination E1 claimed accordingly showed a clearly super-additive, synergistic effect in respect of moisture resistance.

Example 2: The Following Hair Gels were Produced

| Component/raw material | INCI designation or chemical name | V1 | V2 | E1 |
|---|---|---|---|---|
| Aculyn ® 28[1] | Acrylates/beheneth-25 copolymer methacrylate | 4.2 | — | 2.1 |
| AquaStyle SH-100[2] | Acrylates copolymer (and) water | — | 16.5 | 8.25 |
| AMP-ULTRA PC 2000 | Aminomethyl propanol | 0.12 | 0.3 | 0.21 |
| Water | | 96.68 | 83.2 | 89.44 |
| Total | | 100 | 100 | 100 |

[1] 20 wt. % active substance in water
[2] 30 wt. % active substance in water

The quantities are stated in the table as wt. % of the raw material concerned, related to the total composition.

An HHCR test (High Humidity Curl Retention-Test: 6 hours) was performed on washed Kerling hair strands to determine moisture resistance for the styling agents obtained (average value of determination on 5 hair strands each);

| | V1 | V2 | E1 |
|---|---|---|---|
| HHCR | 73% | 72% | 90% |

The polymer combination E1 claimed accordingly showed a clearly super-additive, synergistic effect in respect of moisture resistance.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:
1. A cosmetic composition for the temporary shaping of keratinous fibers, consisting of:
(a) at least one amphiphilic, anionic acrylate copolymer (a), comprising at least one structural unit (a1) and at least one structural unit (a2),

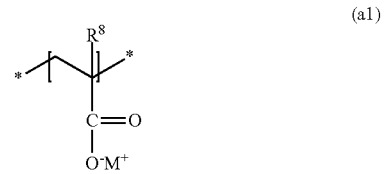

(a1)

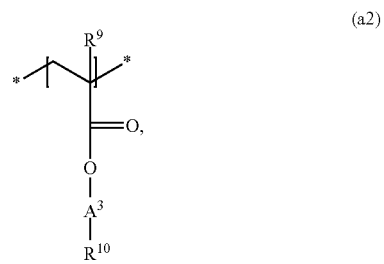

(a2)

wherein

R$^8$ is a hydrogen atom or a methyl group,

R$^9$ is a methyl group,

R$^{10}$ is an octadecyl group,

M$^+$ is a physiologically tolerable cation, and

A$^3$ is a group *—(CH$_2$CH$_2$O)$_x$—*, wherein x is 20, and at least one copolymer (a) comprising at least one structural unit (a1) and at least one structural unit (a2) wherein R$^8$ is a hydrogen atom or a methyl group, R$^9$ is a methyl group, R$^{10}$ is a docosyl group, M$^+$ is a physiologically tolerable cation and A$^3$ is a group *—(CH$_2$CH$_2$O)$_x$—*, wherein x is 25; and (b) at least one anionic acrylate copolymer (b), which is built up of at least the following monomer units;

(b1) at least one acrylic acid unit, (b2) at least one ethyl acrylate unit, (b3) at least one (meth)acrylic acid alkyl ester unit which is different from the (meth)acrylic acid ester unit (b2) and comprises one hydrophobic group as an ester group, at least one alkanolamine; and water in a proportion of at least about 50% by weight with respect to the total weight of the cosmetic composition.

2. Cosmetic composition in accordance with claim 1, wherein the composition comprises copolymer (a) in a fraction of from about 0.05 to about 5.0 wt. % related to the total weight of the cosmetic composition.

3. Cosmetic composition in accordance with claim 1, wherein the composition comprises the anionic acrylate copolymer (b) in a fraction of from about 0.2 to about 2.0 wt. % related to the total weight of the cosmetic composition.

4. Cosmetic composition in accordance with claim 1, wherein the composition takes the form of hair gel, hair spray, hair mousse or hair wax.

5. Cosmetic composition in accordance with claim 1, wherein the composition is utilized for the temporary shaping of keratinous fibers.

6. Method for temporarily shaping keratinous fibers, the method comprising applying the cosmetic composition according to claim 1 to keratinous fibers.

7. Cosmetic composition in accordance with claim 3, wherein the composition comprises the anionic acrylate copolymer (b) in a fraction of from about 1.0 to about 4.0 wt. %.

8. Cosmetic composition in accordance with claim 3, wherein the composition comprises the anionic acrylate copolymer (b) in a fraction of from about 1.5 to about 3.0 wt. %.

9. Cosmetic composition in accordance with claim 1, wherein the anionic acrylate copolymer (a) is a copolymer with the INCI designation acrylates/steareth-20 methacrylate copolymer.

10. Cosmetic composition in accordance with claim 1, wherein the anionic acrylate copolymer (a) is a copolymer with the INCI designation acrylates/beheneth-25 methacrylate copolymer.

* * * * *